United States Patent [19]
Togawa et al.

[11] Patent Number: 5,587,062
[45] Date of Patent: Dec. 24, 1996

[54] SAMPLE COLLECTING APPARATUS BY GEL ELECTROPHORESIS

[75] Inventors: Yoshiyuki Togawa, Osaka; Makoto Miura, Kyoto, both of Japan

[73] Assignee: Shimadzu Corporation, Japan

[21] Appl. No.: 592,872

[22] Filed: Jan. 24, 1996

[51] Int. Cl.$^6$ .................. G01N 27/26; G01N 27/447
[52] U.S. Cl. .................. 204/613; 204/456; 204/462; 204/465; 204/608; 204/615; 204/616
[58] Field of Search .................. 204/606, 607, 204/608, 612, 613, 614, 615, 616, 617, 618, 456, 457, 461, 462, 463, 464, 465

[56] References Cited

U.S. PATENT DOCUMENTS

| 5,217,591 | 6/1993 | Gombocz et al. | 204/616 X |
| 5,384,022 | 1/1995 | Rajasekaran | 204/616 |
| 5,445,723 | 8/1995 | Camacho | 204/614 |

FOREIGN PATENT DOCUMENTS

| 555145 | 8/1993 | European Pat. Off. . |
| 5-223780 | 8/1993 | Japan . |

OTHER PUBLICATIONS

Sergey F. Zakharov, Mark M. Garner, & Andreas Chrambach "Recovery of SDS–protein and DNA using commercial automated gel electrophoresis apparatus" Applied and Theoretical Electrophoresis, vol. 5, (Sep. 1995) 25–29.

*Primary Examiner*—Donald R. Valentine
*Assistant Examiner*—John S. Starsaki, Jr.
*Attorney, Agent, or Firm*—Majestic, Parsons, Siebert & Hsue

[57] ABSTRACT

An apparatus for collecting samples by gel electrophoresis has a base table, a cutting tool or an extractor disposed above the base table, a moving mechanism, a pattern detector and a control device. The base table is for placing thereon a gel in the form of a slab with one of its sandwiching support plates removed therefrom in such a way that the gel is exposed in the upward direction. The cutter is for cutting out a specified portion of the gel, and the extractor is for extracting a specified migration band in such a specified portion of the gel by electrophoresis. The moving mechanism is for moving the cutter, or the extractor, three-dimensionally. The pattern detector is for optically detecting migration patterns in the gel on the base table so as to enable the user to determine which part of the gel or which migration band thereon is of interest. The control device controls the motion of the moving mechanism so as to have a portion of the gel at a specified migration band to be automatically or manually cut out or to have its migration band extracted by electrophoresis.

13 Claims, 4 Drawing Sheets

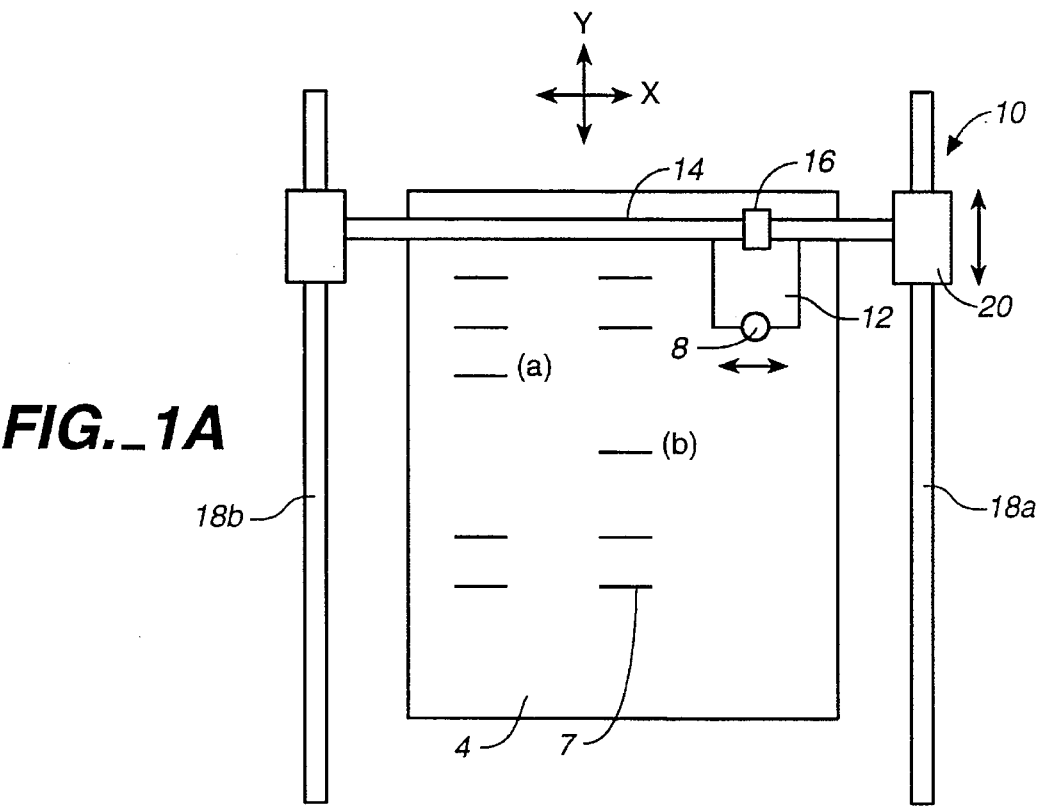
FIG._1A
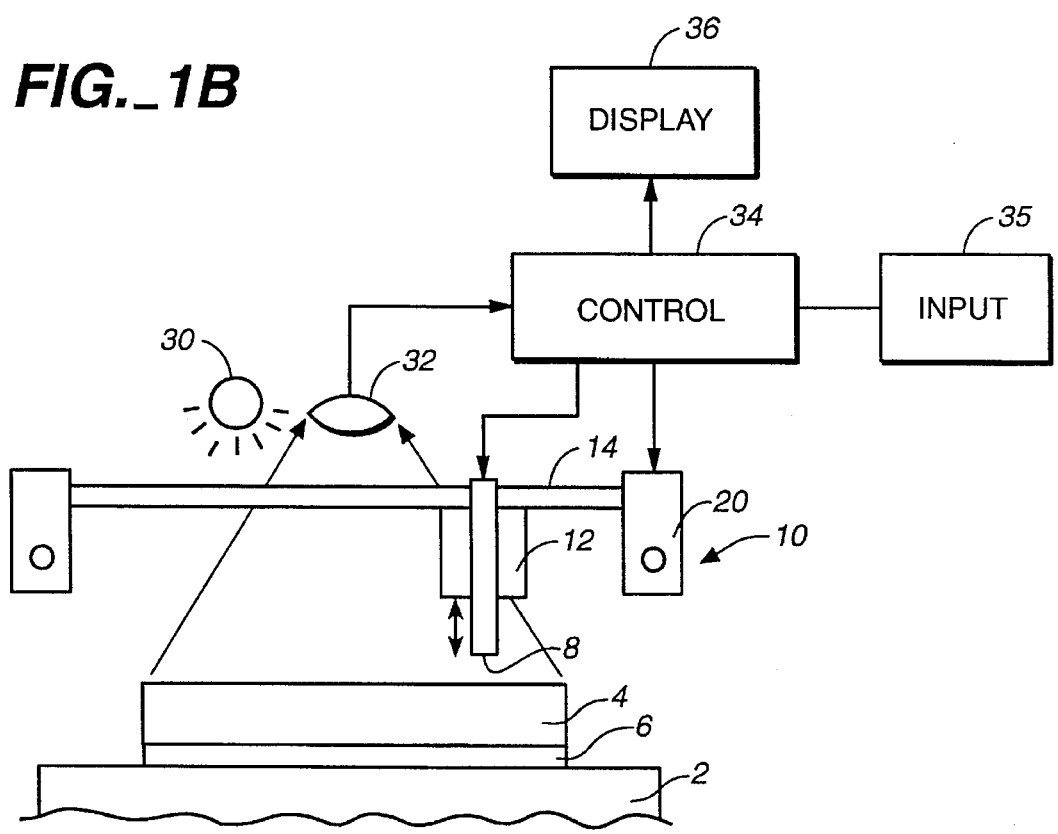
FIG._1B

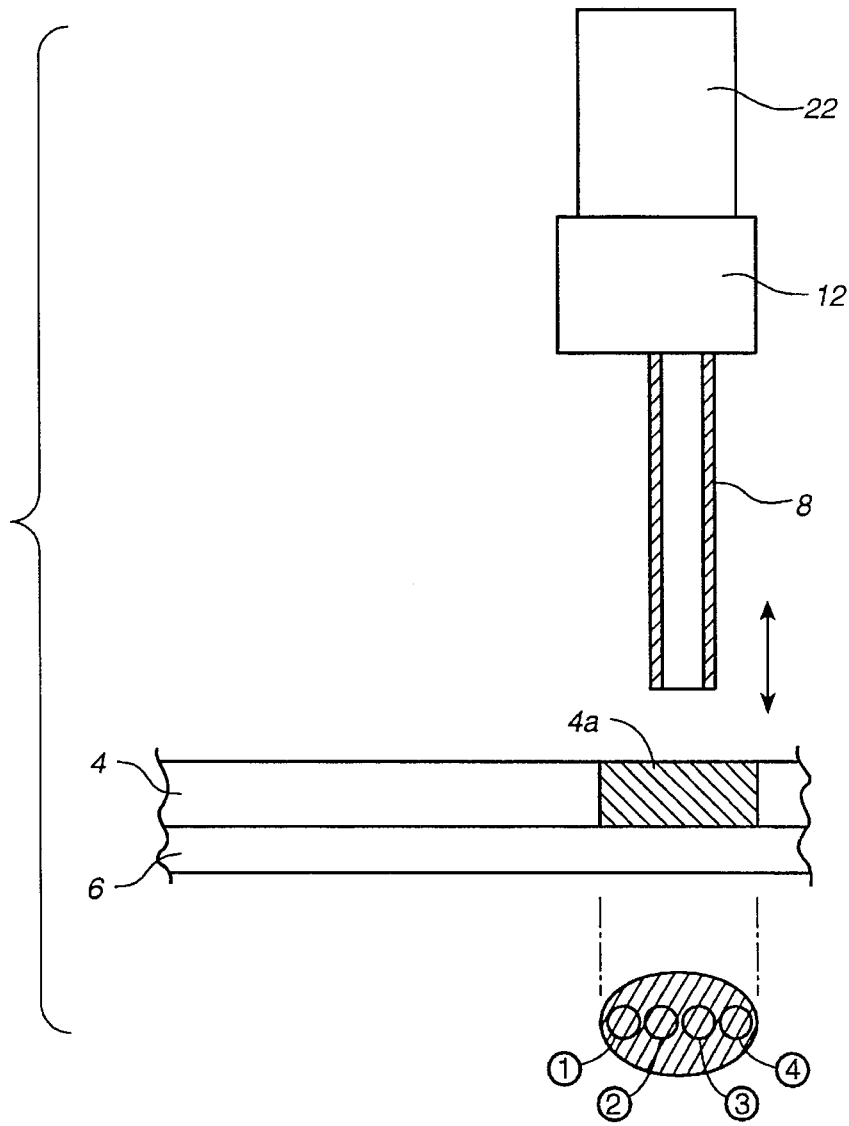
FIG._2A
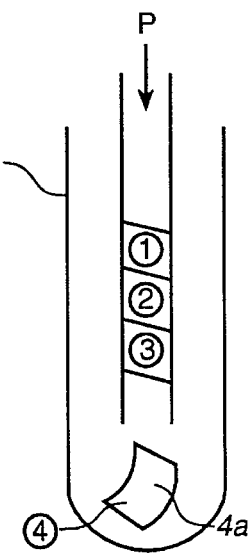
FIG._2B

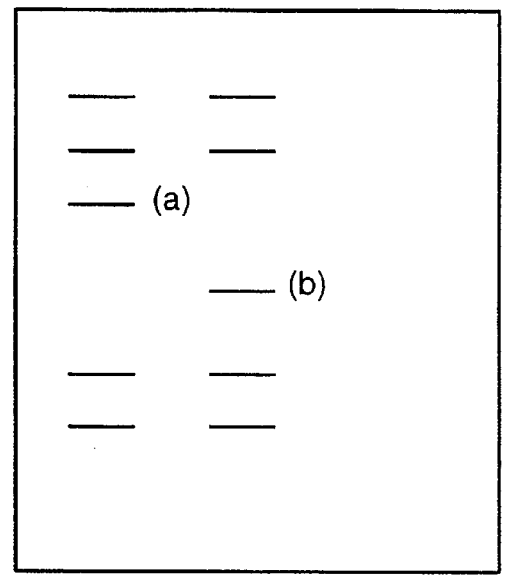
FIG._3A
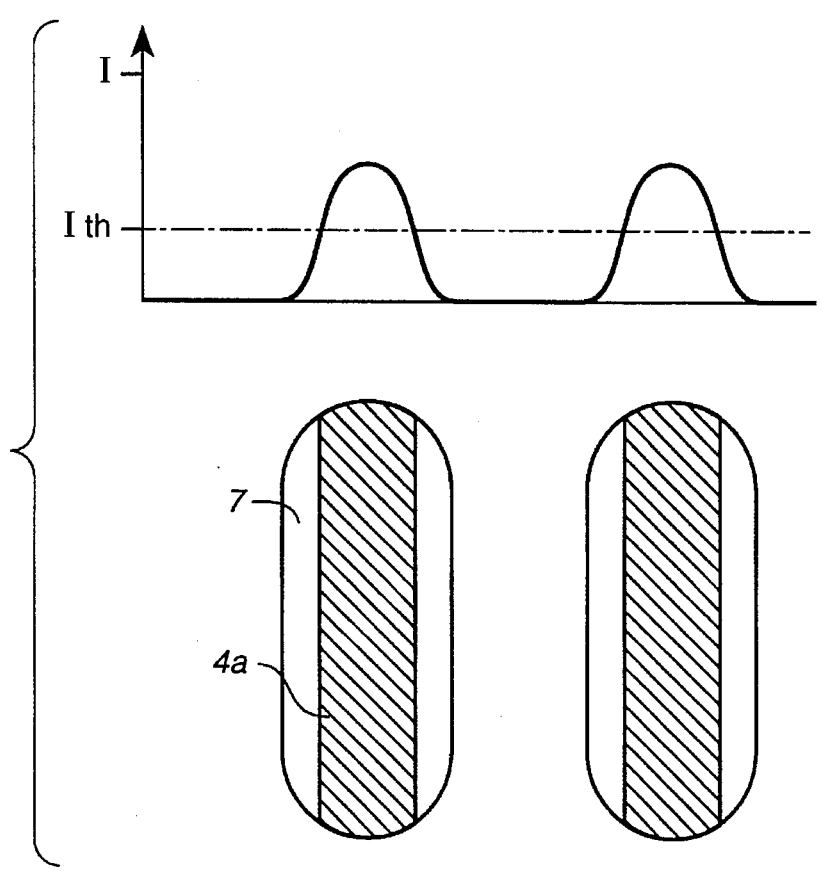
FIG._3B

SAMPLE COLLECTING APPARATUS BY GEL ELECTROPHORESIS

BACKGROUND OF THE INVENTION

This invention relates to an apparatus in the field of life sciences for collecting a specified fraction of a high molecular sample, such as DNA and protein, separated by a gel electrophoresis apparatus.

In the field of genetic engineering, for example, it is frequently required not only to carry out gel electrophoresis of both a standard sample and a target sample to detect their difference by comparing their migration patterns but also to determine the molecular sequence of the part where a difference is detected. For such a purpose, it is necessary to selectively collect a part of the target sample with a migration pattern different from that of the standard sample. Examples of prior art collection method for such a purpose included manually and directly cutting out the gel of the fraction part corresponding to the pattern of the target sample subjected to gel electrophoresis by using a scalpel or to first transfer the developed migration pattern onto a nylon membrane and to then cut this nylon membrane by using a pair of scissors or a scalpel.

In summary, migration patterns are optically analyzed by another apparatus and a desired fraction part is cut out and collected on the basis of information obtained therefrom. Since the analysis of migration patterns and the cutting of a fraction part for collection are two mutually independent and separate operations, the position of the gel to be cut must be ascertained again when this operation is actually performed even if the fraction part to be cut is initially determined by the apparatus for analyzing the migration patterns. Moreover, the manual procedure of cutting by using a scalpel or the like is a cumbersome operation.

SUMMARY OF THE INVENTION

It is therefore an object of this invention to provide an apparatus with which not only can migration patterns be analyzed but also a specified fraction part can be collected or the corresponding migration band can be extracted accurately and easily.

An apparatus embodying this invention, with which the above and other objects can be accomplished, may be characterized as comprising a base table, a cutting tool or an extractor disposed above the base table, a moving mechanism, a pattern detector and a control device. The base table is for placing thereon a gel in the form of a slab with one of its sandwiching support plates removed therefrom in such a way that the exposed gel is facing upward. The cutter is for cutting out a specified portion of the gel, and the extractor is for extracting by electrophoresis a specified migration band in such a specified portion of the gel. The moving mechanism is for moving the cutter, or the extractor, three-dimensionally, that is, along the X and Y axes which define a horizontal plane and along the Z axes which is perpendicular to the surface of the planar gel. The pattern detector is for optically detecting migration patterns in the gel placed on the base table. The control device is for controlling the motion of the moving mechanism so as to have a portion of the gel at a specified migration band to be automatically or manually cut out or to have its migration band extracted.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1A is a plan view of an apparatus embodying this invention, and FIG. 1B is its schematic side view serving also as a block diagram of its control;

FIG. 2A is a schematic sectional side view of the cutting tool, and FIG. 2B is a schematic sectional side view for showing the process of discharging portions of a gel from the tubular part of the cutting tool into a container;

FIG. 3A is an example of displayed image data, and FIG. 3B shows an intensity signal and areas to be cut out;

DETAILED DESCRIPTION OF THE INVENTION

Figure 4:
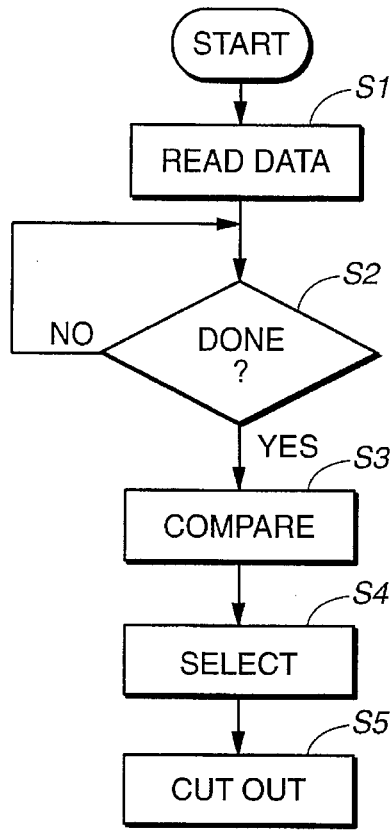
FIG. 4 is a flow chart showing schematically the operation by the control device of FIG. 1B.

An apparatus embodying this invention is described next with reference to FIGS. 1A and 1B. It will be assumed that gel electrophoresis has already been carried out, say, by using a gel of polyacrylamide or agarose in the form of a slab and supported between two glass plates. After the electrophoresis, one of the glass plates sandwiching the gel is removed, and the gel is placed on a base table 2 such that the other of the glass plates is underneath the gel. In FIG. 1B, the planar gel is indicated by numeral 4 and the remaining glass plate, which has not been removed, is indicated by numeral 6. As schematically shown in FIG. 1A, the gel 4 shows patterns of migration bands 7 formed by the electrophoresis of samples, the pattern developed in the left-hand lane being that of a standard sample and that in the right-hand lane being that of a target sample. Above the base table 2 are disposed a cutting tool 8 for cutting and collecting a specified portion of the gel 4 and a cutter-moving mechanism 10 for allowing the cutting tool 8 to move not only in mutually perpendicular horizontal X and Y directions parallel to the surface of the base table 2 but also in the vertical Z direction perpendicular thereto such that a specified portion of the gel 4 can be cut and collected by the cutting tool 8. The cutter-moving mechanism 10 includes a Z-direction driver 12 for supporting the cutting tool 8 and moving it in the Z-direction, that is, in the direction of the thickness of the gel 4, an X-direction driver 16 adapted to move the Z-direction driver 12 along an X-direction guide shaft 14 extending in the X-direction, and a Y-direction driver 20 adapted to move the X-direction guide shaft 14 along a pair of Y-direction guide shafts 18a and 18b extending in the Y-direction.

The cutting tool 8 has a tubular part, as shown in FIG. 2A. Its open bottom end is adapted to be pressed against the gel 4 such that the gel can become packed inside. As the cutting tool 8 is moved horizontally (in the X and Y directions) within a specified areal part 4a of the gel 4 and vertically (along the Z-direction, as indicated by double-headed arrow) up and down to press it against the gel 4, the specified areal part 4a thereof can be packed inside the cutting tool 8. According to the example shown in FIG. 2A, the cutting tool 8 has been moved up and down four times to collect parts indicated by ①–④ from the specified areal part 4a and to sequentially pack them inside the cutting tool 8. A discharge mechanism 22 is provided above the cutting tool 8 to provide compressed air. After the tubular part of the cutting tool 8 is inserted into or moved to a position above a specified container 24, as shown in FIG. 2B, the gel packed inside the tubular part of the cutting tool 8 is discharged into the container 24 as compressed air is supplied (indicated schematically by letter P) from the discharge mechanism 22.

With reference again to FIGS. 1A and 1B, there are provided above the base table 2 a light source 30 such as a laser source or an ultraviolet light source for irradiating the gel 4 placed on the base table 2 and an optical detector 32 such as a photoelectric multiplier or a semiconductor detector for optically detecting the migration patterns developed in the gel 4. In other words, the light source 30 and the optical detector 32 comprise together a migration pattern detecting means. Numeral 34 indicates a control device for specifying a migration pattern to be cut out on the basis of a detection signal outputted from the optical detector 32 and controlling the process of cutting out the gel 4 through the cutter-moving mechanism 10. For this purpose, the control device 34 collects data on each data line, as shown at S1 in the schematic flow chart of FIG. 4, until data on all lines have been taken (YES in S2), compares the migration pattern of the standard sample with the migration pattern of the target sample (S3), selects a specific migration band of the target sample with a particular pattern (S4) and controls the motion of the X-direction driver 16, the Y-direction driver 20 and the Z-direction driver 12 to cut out a portion corresponding to the specified migration band (S5). Numeral 36 indicates a display device for displaying a migration pattern such as a cathode ray tube adapted to display image data as shown in FIG. 3A on a display screen.

Let us assume now that image data as shown in FIG. 3A have been detected by the control device 34 (serving also as means for analyzing migration patterns). Let us assume further that the migration band indicated as (b) in the pattern from the target sample is a particular band to be cut out in view of the migration band indicated by (a) in the pattern from the standard sample. The recognition that the migration band (b) is the particular migration band of interest may be carried out automatically by a computer program, or it may be left to the operator to watch the images displayed on the display device 36 and to input this information manually through an input means (schematically shown at 35 in FIG. 1B) to the control device 34.

In situations where the control device 34 automatically specifies an area to be cut out, as described above with reference to FIG. 4, it may be adapted to optically analyze the degree of planar intensity of the migration band, to set a threshold value $I_{th}$ for the intensity signal I, as shown in FIG. 3B, and to determine the shaded portion of the image to be the target area 4a to be cut out.

After particular one of the migration bands 7 of the gel 4 has been thus determined, whether automatically or by the operator watching the display device 36, the cutting tool 8 is transported to a position thereabove, the Z-direction driver 12 moves the cutting tool 8 vertically up and down, and the X-direction driver 16 and the Y-direction driver 20 move the cutting tool 8 in a coordinated manner inside each target area 4a such that the gel in the target area 4a can be packed inside the tubular part of the cutting tool 8. Desired sample fractions of the gel parts 4a can thus be packed in the cutting tool 8.

Although a cutting tool with a tubular part, as described above, is convenient because desired portions of a gel can be cut out and packed simply by moving the cutting tool up and down in the direction of the thickness of the gel, a tubular cutter is not intended to be an indispensable component of an apparatus of this invention. A scalpel may be used to cut out desired portions of a gel.

Figure 5:
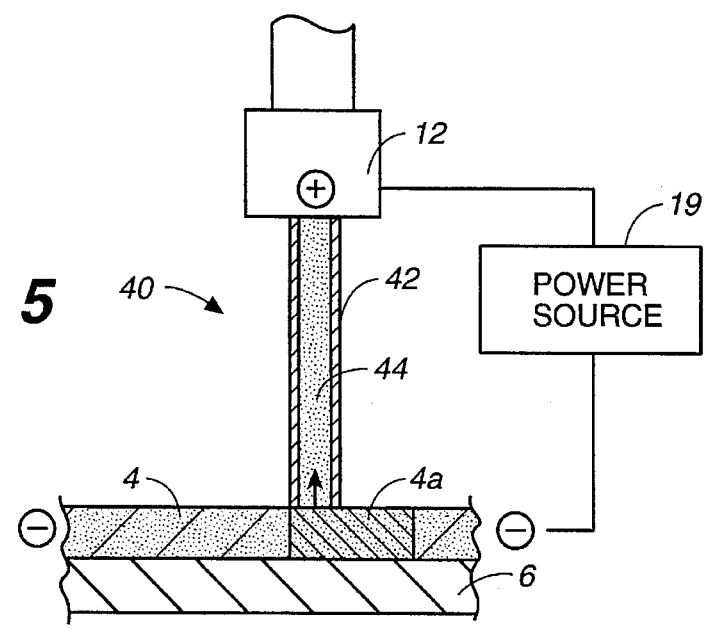
FIG. 5 is a schematic sectional side view of an extractor according to a second embodiment of the invention.

According to a second embodiment of the invention, an extractor 40 such as shown in FIG. 5 replaces the cutting tool 8 of the first embodiment of the invention described above with reference to FIGS. 1 and 2. In FIG. 5, therefore, those components and parts which are substantially similar to those shown above in FIGS. 1 and 2 are indicated by the same numerals. The extractor 40 according to this embodiment of the invention is characterized as having a tubular part 42 attached to the Z-direction driver 12 and filled with a gel or an electrolytic solution 44. An electric power source 19 is provided for extraction by electrophoresis such that a positive potential can be applied to a top end part of the gel or the electrolytic solution 44 inside the tubular part 42 and a negative potential to the gel 4 on the glass plate 6.

When a migration band is to be extracted, the bottom end of the tubular part 42 of the extractor 40 is transported to the position contacting the gel part 4a of the migration band to be extracted, as described above with reference to the first embodiment of this invention, a positive electric potential is applied to the gel or the electrolytic solution 44 inside the tubular part 42 and a negative electric potential is applied to the gel 4. This causes the migration band in the gel part 4a to be extracted into the gel or the electrolytic solution 44 inside the tubular part 42 by electrophoresis. The extracted migration band is discharged into a container 42 together with the gel or the electrolytic solution 44 inside the tubular part 42, as explained above with reference to FIG. 2 for the case of the first embodiment of this invention. Specification of a position for extracting a migration band of the gel 4 and control of the transportation of the extractor 40 are carried out also as described above with reference to the first embodiment of the invention.

Although the invention has been described above with reference to examples wherein a gel in which electrophoresis of a sample has already been completed elsewhere by means of another apparatus is placed on the base table, this is not intended to limit the scope of the invention. An apparatus according to this invention may be adapted to have a gel before electrophoresis to be placed on the base table. In such a case, electric power sources may be disposed at both ends of the gel for applying a migration potential and the procedure of cutting out the gel from a specified area may be carried out after electrophoresis is carried out on the same base table.

Apparatus according to the present invention may be characterized as capable not only of optically detecting migration patterns of a gel after electrophoresis has taken place, moving a cutting tool or an extractor three-dimensionally while the gel is kept in the same condition on a base table and cutting or extracting a desired portion of the gel, but also of carrying them out all in a series of steps without moving the gel itself. As a result, the cutting and extraction can be carried out easily and precisely because they can be done automatically.

What is claimed is:

1. A sample collecting apparatus comprising:

a base table for placing a gel thereon;

a cutting tool disposed above said base table for cutting out a specified part of said gel;

a moving mechanism for moving said cutting tool three-dimensionally for causing said cutting tool to cut out said specified part of said gel;

a detector for optically detecting migration patterns in said gel placed on said base table; and a control device for controlling said moving mechanism according to detection by said detector so as to cause said cutting tool to cut out said specified part of said gel.

2. The sample collecting apparatus of claim 1 wherein said control device automatically controls said moving mechanism.

3. The sample collecting apparatus of claim 1 wherein said gel is in the form of a slab with a top surface, said moving mechanism comprising an X-direction driver and a Y-direction driver each adapted to move said cutting tool parallel to said top surface of said gel and a Z-direction driver for moving said cutting tool perpendicular to said top surface of said gel.

4. The sample collecting apparatus of claim 1 further comprising a display device for displaying thereon an image of migration patterns on said gel.

5. The sample collecting apparatus of claim 4 further comprising an input means for allowing a user to input position data therethrough, said control device controlling said moving mechanism according to said position data inputted through said input means.

6. The sample collecting apparatus of claim 1 wherein said cutting tool includes a tubular part adapted to be compressed against said gel to cut a part thereof.

7. A sample collecting apparatus comprising:

a base table for placing a gel thereon;

an extractor disposed above said base table for extracting by electrophoresis a migration band at a specified part of said gel;

a moving mechanism for moving said extractor three-dimensionally for causing said extractor to extract said migration band at said specified part of said gel;

a detector for optically detecting migration patterns in said gel placed on said base table; and a control device for controlling said moving mechanism according to detection by said detector so as to cause said extractor to extract said migration band at said specified part of said gel.

8. The sample collecting apparatus of claim 7 wherein said control device automatically controls said moving mechanism.

9. The sample collecting apparatus of claim 7 wherein said gel is in the form of a slab with a top surface, said moving mechanism comprising an X-direction driver and a Y-direction driver each adapted to move said cutting tool parallel to said top surface of said gel and a Z-direction driver for moving said extractor perpendicular to said top surface of said gel.

10. The sample collecting apparatus of claim 7 further comprising a display device for displaying thereon an image of migration patterns on said gel.

11. The sample collecting apparatus of claim 10 further comprising an input means for allowing a user to input position data therethrough, said control device controlling said moving mechanism according to said position data inputted through said input means.

12. The sample collecting apparatus of claim 7 wherein said extractor includes a tubular part filled with a gel and having a bottom opening adapted to be positioned in contact with said gel on said base table.

13. The sample collecting apparatus of claim 7 wherein said extractor includes a tubular part filled with an electrolyte and having a bottom opening adapted to be positioned in contact with said gel on said base table.

* * * * *